(12) United States Patent
Kondo et al.

(10) Patent No.: US 7,677,189 B2
(45) Date of Patent: Mar. 16, 2010

(54) MANUFACTURING SYSTEM AND MANUFACTURING METHOD FOR SHEET-LIKE STRUCTURE

(75) Inventors: Hideki Kondo, Kagawa-ken (JP); Masashi Hosokawa, Kagawa-ken (JP)

(73) Assignee: Uni-Charm Corporation, Ehime (JP)

( * ) Notice: Subject to any disclaimer, the term of this patent is extended or adjusted under 35 U.S.C. 154(b) by 495 days.

(21) Appl. No.: 11/669,363

(22) Filed: Jan. 31, 2007

(65) Prior Publication Data

US 2007/0175372 A1  Aug. 2, 2007

(30) Foreign Application Priority Data

Feb. 1, 2006  (JP) .............. 2006-024399

(51) Int. Cl.
*D05B 3/00* (2006.01)
*A61F 13/34* (2006.01)
*D05B 27/00* (2006.01)

(52) U.S. Cl. ............ 112/475.01; 112/475.08; 604/385.18; 28/120

(58) Field of Classification Search ........... 112/475.01, 112/475.06, 475.17, 475.08, 414, 418, 429, 112/430, 439, 470.21, 470.33, 139, 152, 112/320, 427, 132, 144, 145, 146; 289/2; 383/75; 604/14, 385.18; 28/120
See application file for complete search history.

(56) References Cited

U.S. PATENT DOCUMENTS

| 1,920,822 | A | * | 8/1933 | West ............... 112/470.21 |
| 2,532,438 | A |   | 12/1950 | Behr |
| 2,546,623 | A | * | 3/1951 | Abler ..................... 383/75 |
| 2,777,408 | A | * | 1/1957 | Beck ................. 112/470.21 |
| 2,825,474 | A | * | 3/1958 | Coley et al. ............... 414/26 |
| 3,240,176 | A | * | 3/1966 | Morrison ............ 112/475.18 |
| 4,515,097 | A | * | 5/1985 | Rovin ................. 112/475.06 |
| 5,080,030 | A | * | 1/1992 | Taddicken ............... 112/147 |
| 5,556,205 | A | * | 9/1996 | Gallie et al. ............... 383/24 |
| 6,213,040 | B1 | * | 4/2001 | Shepard .............. 112/475.17 |
| 6,585,300 | B1 | * | 7/2003 | Rajala et al. ................ 289/2 |
| 6,887,226 | B2 | * | 5/2005 | Cassoni et al. ....... 604/385.18 |

FOREIGN PATENT DOCUMENTS

| JP | 62-144658 A | 6/1987 |
| JP | 05-9528 A | 2/1993 |
| JP | 05-212075 A | 8/1993 |
| JP | 07-22726 A | 4/1995 |
| JP | 08-117282 A | 5/1996 |

* cited by examiner

*Primary Examiner*—Ismael Izaguirre
(74) *Attorney, Agent, or Firm*—Brinks Hofer Gilson & Lione

(57) ABSTRACT

An object of the present invention is to provide a manufacturing system and a method for manufacturing sheet-like structures. The manufacturing system of sheet-like structures contains a loosened portion forming apparatus by which plural loosened portions, which are substantially U-shaped, are formed on a cord member, and plural linear portions, which connect each of the plural loosened portions, are formed substantially linearly; and a sewing apparatus by which each of the plural absorbing members and each of the plural linear portions are sewn with a thread member.

14 Claims, 10 Drawing Sheets

MANUFACTURING SYSTEM AND MANUFACTURING METHOD FOR SHEET-LIKE STRUCTURE

This application is based on and claims the benefit of priority from Japanese Patent Application No. 2006-024399, filed on Feb. 1, 2006, the content of which is incorporated herein by reference.

BACKGROUND OF THE INVENTION

1. Field of the Invention

The present invention relates to manufacturing systems and methods for manufacturing sheet-like structures comprising sheet members with prescribed forms and predefined cord members.

2. Related Art

Conventionally, in sewing sheet-like structures in which predefined cord members are sewn onto sheet members of a prescribed form, cord members and the sheet members are sewn together in a longitudinal direction of the cord members in order to sew the cord members and sheet members firmly. When a large quantity of sheet-like structures are manufactured continuously for example, a cord member is reeled out linearly and sewn continuously with a thread while plural sheet members are arranged at predetermined intervals so as to be in contact with the cord member. The cord member placed so as to connect each sheet member is cut to obtain prescribed sheet-like structures. In this case, a sewn area which continued from the area sewn with the sheet members is formed on the cord member with a thread member. This has caused problems in that, for example, the thread member starts to come off from free ends of the cord member in the sheet-like structures causing the thread member sewn onto the sheet member to also come off.

In order to solve the above problems, an absorbing member for tampons, which is sewn from the tail end that is a free end of the cord member toward the leading end that is the sheet-like absorbing member, with a double chain stitch for preventing the threads from coming off and for preventing separation between cord members and sheet members caused by the coming off of the threads, is disclosed in Japanese Registered Utility Model No. 2534839 (referred to as "Patent Document 1" below).

In the absorbing member stated in Patent Document 1, sewing starts from a free end of the cord member that is the tail end of the cord member toward the absorbing member that is the leading end is performed with a double chain stitch, thereby the thread is prevented from coming off by using a characteristic of the double chain stitch. That is, the double chain stitch has a characteristic in which when the seam at the tail end comes undone and only a bobbin thread is pulled off from the sewing end, the bobbin thread may come off and the whole seam may come undone; however, when the bobbin thread is pulled off from the threshold, the whole seam does not come undone. The whole thread members can be protected from coming undone as a result of the thread coming off from the free end of the extended portion that is the tail end of the absorbing member stated in Patent Document 1 by using the above characteristic of the double chain stitch.

However, the above thread coming off cannot be prevented completely in the absorbing member of Patent Document 1 because the thread member runs from the sheet member to the cord member continuously. Also, when this is used as an absorbing member for tampons, menstrual blood may leak from the free end side of the extended portion through the thread. In addition, the sewn area is formed continuously from the leading end of the absorbing member to the tail end that is a free end of the extended portion of the cord member, in the manufacturing process. Consequently, this still offer problems in that the thread is used more than necessary and the step of sewing requires excessive time. These are problems to be solved by the present invention.

SUMMARY OF THE INVENTION

In view of the abovementioned problems, an object of the present invention is to provide a manufacturing system and a method for manufacturing sheet-like structures comprising a sheet member with a prescribed form, and a cord member which is sewn onto a predefined surface of the sheet member with a specified thread member, which has an extended portion extending from an outer edge of the predefined surface, and on which a non-sewn area, without the specified thread member, is formed.

The present inventors have found a manufacturing system and a method for manufacturing that is suitable for sheet-like structures comprising a sheet member with a prescribed form and a cord member which is sewn onto a predefined surface of the sheet member with a specified thread member, which has an extended portion extending from an outer edge of the predefined surface, and on which a non-sewn area, not including the specified thread member, is formed.

A first aspect of the present invention provides a manufacturing system for a sheet-like structure comprising: a sheet member with a prescribed form; and a cord member sewn onto a predefined surface of the sheet member with a specified thread member and having an extended portion extending from an outer edge of the predefined surface on which a non-sewn area without the specified thread member is formed; the system comprising: a loosened portion forming apparatus to form plural loosened portions on a cord member reeled out in a specified direction, the loosened portions are substantially U-shaped and extending in the direction different to a specified direction, and plural substantially linear portions which connect each of the plural loosened portions respectively; an arranging apparatus to arrange each of the plural sheet members so as to be in contact with each of the plural linear portions formed by the loosened portion forming apparatus; a sewing apparatus to sew each of the plural sheet members arranged by the arranging apparatus and each of the plural linear portions which come in contact with the plural sheet members with a thread member; a thread member cutting apparatus to cut thread connecting portions which are parts of the thread member formed so as to connect a specified sheet member of the plural sheet members on which each of the plural linear portions are sewn by the sewing apparatus and other sheet members which lie adjacent to the specified sheet member; and a cord member cutting apparatus to cut cord connecting portions which are parts of the cord member formed so as to connect a specified sheet member of the plural sheet members and other sheet members which lie adjacent to the specified sheet member at a specified position.

According to the first aspect of the present invention, a manufacturing system for a sheet-like structure comprising: a sheet member with a prescribed form; and a cord member sewn onto a predefined surface of the sheet member with a specified thread member and having an extended portion extending from an outer edge of the predefined surface on which a non-sewn area without the specified thread member is formed comprises: a loosened portion forming apparatus to form plural loosened portions on a cord member reeled out in a specified direction, the loosened portions are substantially U-shaped and extending in the direction different to a specified direction, and plural substantially linear portions which connect each of the plural loosened portions respectively; an arranging apparatus to arrange each of the plural sheet members so as to be in contact with each of the plural linear portions formed by the loosened portion forming apparatus; a sewing apparatus to sew each of the plural sheet members arranged by the arranging apparatus and each of the plural linear portions which come in contact with the plural sheet members with a thread member; a thread member cutting apparatus to cut thread connecting portions which are parts of the thread member formed so as to connect a specified sheet member of the plural sheet members on which each of the plural linear portions are sewn by the sewing apparatus and other sheet members which lie adjacent to the specified sheet member; and a cord member cutting apparatus to cut cord connecting portions which are parts of the cord member formed so as to connect a specified sheet member of the plural sheet members and other sheet members which lie adjacent to the specified sheet member at a specified position.

The manufacturing target of the manufacturing systems according to the present invention is a sheet-like structure containing a sheet member with a prescribed form and a cord member which is sewn onto a predefined surface of the sheet member with a specified thread member, and has an extended portion extending from an outer edge of the predefined surface on which a non-sewn area, without the specified thread member, is formed. The sheet member of the sheet-like structure is a substantially sheet-like member made of a material on which cord members can be sewn with a specified thread member, and examples include fabric members, rubber members, and sheet-like absorbing members, which make up the above-mentioned absorbing member for tampons. The cord member sewn onto the sheet member is made of a material which can be sewn onto the sheet members, and examples include strings made of natural or synthesized fibers, resin-made cords, threads larger than a specified diameter, and composite yarns formed by twisting a number of above threads. Moreover, the thread member may be finer than the specified diameter, formed of a material with which the sheet member and the cord member can be sewn together, and examples include threads formed of natural materials, threads of synthesized fibers and fine wires.

The loosened portion forming apparatus forms plural loosened portions on a cord member reeled out in a specified direction from a thread supplying unit in which thread members are winded up. The loosened portions are substantially U-shaped and extend in a direction different to a specified direction. Further, the loosened portion forming apparatus forms plural linear portions which connect, substantially linearly, each of the formed plural loosened portions respectively. These loosened portions become extended portions of the sheet-like structure and the linear portions become portions sewn onto the sheet members.

The arranging apparatus arranges each of the plural sheet members so as to be in contact with each of the plural linear portions formed by the loosened portion forming apparatus. By arranging as above, continuous sewing by a sewing apparatus as described below becomes possible.

The sewing apparatus sews each of the plural sheet members arranged by the arranging apparatus and each of the plural linear portions, which is in contact with the plural sheet members, with a thread member. For example, sheet-like members and a cord member are sewn together by sewing along the cord member arranged in contact with the sheet members continuously by means of a specified sewing machine while loosened portions of the cord member are not sewn. By the above procedure, non-sewn areas can be formed on the cord member which make up the loosened portions that will be extended portions.

The thread member cutting apparatus cuts thread connecting portions which are parts of the thread member formed so as to connect a specified sheet member of the plural sheet members on which each of the plural linear portion is sewn by the sewing apparatus and other sheet members which lie adjacent to the specified sheet member. In addition, the cord member cutting apparatus cuts cord connecting portions, which are parts of the cord member formed so as to connect a specified sheet member of the plural sheet members and other sheet members which lie adjacent to the specified sheet member, at a specified position. The order of above cutting steps by the thread member cutting apparatus and the cord member cutting apparatus is not specified and may be performed simultaneously. For example, the thread member cutting apparatus and the cord member cutting apparatus may be the same cutting unit by which the thread connecting portions and the cord connecting portions are cut simultaneously.

Examples of the thread member cutting apparatus and the cord member cutting apparatus include specified cutter members and roll members on which convex a blade is formed on a predefined surface.

The manufacturing system may comprise a cord member reeling-out apparatus to reel out the cord member in the specified direction.

By comprising a cord member reeling-out apparatus to reel out the cord member in the specified direction, thread members can be supplied continuously in a specified direction.

The loosened portion forming apparatus may configured to arrange the plural linear portions substantially linearly at specified intervals.

By making the loosened portion forming apparatus to arrange the plural linear portions substantially linearly at specified intervals, sewing can be performed easily by a sewing apparatus.

The sewing apparatus may be configured to sew each of the plural linear portions, arranged substantially linearly at specified intervals by the loosened portion forming apparatus, onto each of the plural sheet members along a straight line formed by the plural linear portions.

As the sewing apparatus is configured to sew each of the plural linear portions, arranged substantially linearly at specified intervals by the loosened portion forming apparatus, onto each of the plural sheet members along a straight line formed by the plural linear portions, sewing can be performed easily by a sewing apparatus and allows precise sewing to be performed continuously.

The cord member cutting apparatus may comprise an apparatus configured to extend the cord connecting portions substantially linearly.

As the cord member cutting apparatus comprises an apparatus configured to extend the cord connecting portions substantially linearly, the cord member which makes up the cord connecting portions can be cut easily, and the lengths of the extended portions formed by the cord connecting portions can be made constant.

The sheet-like structure further may comprise a sewn area formed on a free end side of the extended portion and including a predefined thread member and the loosened portion forming apparatus may be configured to lengthen each length of the plural linear portions in a specified direction to be longer than the length along the specified direction of the plural sheet members which are arranged in contact with the respective plural linear portions by the arranging apparatus.

According to the above embodiment, the sheet-like structure further comprises a sewn area formed on a free end side of the extended portion and including a predefined thread member. The loosened portion forming apparatus is configured to lengthen each length of the plural linear portions in a specified direction to be longer than the length along the specified direction of the plural sheet members which are arranged in contact with the respective plural linear portions by the arranging apparatus. In this way, the cord member can be sewn onto the sheet member by sewing along the linear portions by the sewing apparatus while the sheet members are arranged in contact with the linear portions, and the areas sewn with a specified thread member can also be formed on the portions extended from the sheet members in contact with the linear portions. A specified portion of the sewn areas is cut, thereby enabling sewn areas containing the specified thread member to be formed on free ends of the extended portions of the sheet members which lie adjacent to the above sheet member.

The sheet member may be a sheet-like absorbing member comprising a specified absorbing layer with liquid absorbability coated with a surface material of thin film form, and the manufacturing system for the sheet-like structure further comprises a sheet-like member forming apparatus to apply the surface material to the absorbing layer.

According to the above manufacturing system for a sheet-like structure sheet member, a sheet-like absorbing member comprising a specified absorbing layer with liquid absorbability coated with a surface material of thin film form, and the manufacturing system for the sheet-like structure further comprises a sheet-like member forming apparatus to apply the surface material to the absorbing layer. This enables a sheet-like absorbing member to be formed by applying a surface material to the fibrous absorbing layer for preventing unraveling of the fibrous absorbing layer, and enables the above-mentioned cord member to be sewn onto the absorbing member formed in a sheet-like form.

The second aspect of the present invention provides a method for manufacturing a sheet-like structure, containing: a sheet member with a prescribed form; and a cord member sewn onto a predefined surface of the sheet member with a specified thread member and having an extended portion extended from an outer edge of the predefined surface on which a non-sewn area without the specified thread member is formed; the method comprising steps of: forming plural loosened portions on a cord member reeled out in a specified direction, the loosened portions are substantially U-shaped and extending in the direction different to a specified direction, and plural linear portions which connect each of the plural loosened portions respectively, substantially linearly; arranging each of the plural sheet members so as to be in contact with the respective plural linear portions formed in the step of forming the loosened portions; sewing each of the plural sheet members arranged in the arranging step and each of the plural linear portions which come in contact with the plural sheet members with a thread member; cutting thread connecting portions which are parts of the thread member formed so as to connect a specified sheet member of the plural sheet members on which each of the plural linear portion are sewn in the sewing step and other sheet members which lie adjacent to the specified sheet member; and cutting cord connecting portions which are parts of the cord member formed so as to connect a specified sheet member of the plural sheet members and other sheet members which lie adjacent to the specified sheet member at a specified position.

According to the second aspect, the method for manufacturing a sheet-like structure, containing: a sheet member with a prescribed form; and a cord member sewn onto a predefined surface of the sheet member with a specified thread member and having an extended portion extended from an outer edge of the predefined surface on which a non-sewn area without the specified thread member is formed; comprises steps of: forming plural loosened portions on a cord member reeled out in a specified direction, the loosened portions are substantially U-shaped and extending in the direction different to a specified direction, and plural linear portions which connect each of the plural loosened portions respectively, substantially linearly; arranging each of the plural sheet members so as to be in contact with the respective plural linear portions formed in the step of forming the loosened portions; sewing each of the plural sheet members arranged in the arranging step and each of the plural linear portions which come in contact with the plural sheet members with a thread member; cutting thread connecting portions which are parts of the thread member formed so as to connect a specified sheet member of the plural sheet members on which each of the plural linear portion are sewn in the sewing step, and other sheet members which lie adjacent to the specified sheet member; and cutting cord connecting portions which are parts of the cord member formed so as to connect a specified sheet member of the plural sheet members and other sheet members which lie adjacent to the specified sheet member at a specified position.

The method for manufacturing according to the present invention is directed towards manufacturing a sheet-like structure containing a sheet member with a prescribed form and a cord member that is sewn onto a predefined surface of the sheet member with a specified thread member, and has an extended portion extending from an outer edge of the predefined surface on which a non-sewn area, without the specified thread member, is formed. The sheet member of the sheet-like structure is a substantially sheet-like member made of a material on which cord members can be sewn with a specified thread member, and examples include fabric members, rubber members, and sheet-like absorbing members which make up the above-mentioned absorbing member for tampons. The cord member sewn onto the sheet member is made of a material which can be sewn onto the sheet members, and examples include strings made of natural or synthesized fibers, resin-made cords, threads of more than specified diameter and composite yarns formed by twisting number of above threads. Moreover, the thread member is a member which is finer than a specified diameter and formed of a material which can sew the sheet member and the cord member together, and examples include threads formed of natural materials, threads of synthesized fibers and fine wires.

In a step of forming the loosened portion, plural loosened portions, which are substantially U-shaped and extend in a direction different to a specified direction, are formed on a cord member reeled out in the specified direction from a thread supplying unit in which thread members are winded up. Plural linear portions, which connect each of the plural loosened portions respectively, are formed substantially linearly. These loosened portions become extended portions of the sheet-like structure and the linear portions become portions sewn onto the sheet member.

In a step of arranging, each of the plural sheet members are arranged so as to be in contact with each of the plural linear portions formed in the forming the loosened portion. By arranging as above, continuous sewing is possible in a step of sewing, as described below.

In the step of sewing, each of the plural sheet members arranged in the step of arranging and each of the linear portions which come in contact with each of the plural sheet members are sewn together with a thread member. For example, sheet-like members and a cord member are sewn together by sewing continuously along the cord member which is in contact with the sheet members by means of a specified sewing machine while loosened portions of the cord member are not sewn. In this way, non-sewn areas can be formed on the cord member which makes up the cord connecting portions that will form extended portions.

The thread connecting portions, which are parts of a thread member formed so as to connect the specified sheet member of the plural sheet members on which each of the linear portions are sewn in the step of sewing and other sheet members which lie adjacent to the specified sheet member, are cut in the step of cutting the thread member. In addition, cord connecting portions, which are parts of a cord member formed so as to connect a specified sheet member of the plural sheet members and the sheet members which lie adjacent to the specified sheet member, are cut at a specified position in the step of cutting the cord member. The order of steps of cutting the thread member and cutting the cord member is not specified and may be performed simultaneously. For example, the thread member cutting apparatus in the cutting the thread member and the cord member cutting apparatus in the cutting the cord member may be the same cutting unit and the thread connecting portions and the cord connecting portions may be cut simultaneously.

The steps of cutting the thread member and cutting the cord member may be exemplified by cutting steps performed by specified cutter members and roll members on which a convex blade is formed on a predefined surface.

The method for manufacturing a sheet-like structure may further comprises reeling-out a cord member wherein the cord member is reeled out in the specified direction.

According to the method for manufacturing a sheet-like structure, reeling-out a cord member wherein the cord member is reeled out in the specified direction is comprised. This enables the thread member to be supplied continuously in a predefined direction.

The step of forming the loosened portions may comprise arranging the plural linear portions substantially linearly at specified intervals.

According to the method for manufacturing a sheet-like structure, the step of forming the loosened portions may arrange the plural linear portions substantially linearly at specified intervals. This enables sewing to be performed easily in the step of sewing.

Each of the plural linear portions, arranged substantially linearly at specified intervals in the step of forming the loosened portions, may be sewn onto each of the plural sheet members along a straight line formed by the plural linear portions in the sewing step.

According to the method for manufacturing a sheet-like structure, each of the plural linear portions, arranged substantially linearly at specified intervals in the step of forming the loosened portions, is sewn onto each of the plural sheet members along a straight line formed by the plural linear portions in the sewing step. This enables sewing to be performed easily in the step of sewing and allows precise sewing to be performed continuously.

The step of cutting the cord member may comprise extending the cord connecting portions substantially linearly.

According to the method for manufacturing a sheet-like structure, step of cutting the cord member is comprise extending the cord connecting portions substantially linearly. This enables the cord member, which makes up the cord connecting portions, to be cut easily, and the lengths of the extended portions formed by the cord connecting portions to be made constant.

The sheet-like structure may comprise a sewn area formed on a free end side of the extended portion and including a predefined thread member and in the step of forming the loosened portions, each length of the linear portions is lengthened in a specified direction, to be longer than the length of the sheet members, which are arranged in contact with the cord member by the arranging apparatus.

According to the method for manufacturing a sheet-like structure, the sheet-like structure comprises a sewn area formed on a free end side of the extended portion and including a predefined thread member and in the step of forming the loosened portions, each length of the linear portions is lengthened in a specified direction, to be longer than the length of the sheet members, which are arranged in contact with the cord member by the arranging apparatus. In this way, the cord member can be sewn onto the sheet member by sewing along the linear portions in the step of sewing while the sheet members are arranged in contact with the linear portions, and the areas sewn with a specified thread member can be formed on the portions extending from the sheet members in contact with the linear portions. A specified portion of the sewn areas is cut, thereby enabling sewn areas containing the specified thread member to be formed on free ends of the extended portions of the sheet members which lie adjacent to the sheet member.

The sheet member may be a sheet-like absorbing member comprising a specified absorbing layer with liquid absorbability coated with a surface material of thin film form, and the method for manufacturing sheet-like structures further comprises forming a sheet-like member in which the surface material is applied to the absorbing layer.

According to the method for manufacturing a sheet-like structure, the sheet member is a sheet-like absorbing member comprising a specified absorbing layer with liquid absorbability coated with a surface material of thin film form, and the method for manufacturing sheet-like structures further comprises forming a sheet-like member in which the surface material is applied to the absorbing layer. This allows a sheet-like absorbing member to be formed by applying a surface material to the fibrous absorbing layer for preventing unraveling of the fibrous absorbing layer, and enables the above-mentioned cord member to be sewn onto the absorbing member formed in a sheet-like form.

The present invention can provide a manufacturing system and a method for manufacturing sheet-like structures containing a sheet member with a prescribed form and a cord member that is sewn onto a predefined surface of the sheet member with a specified thread member and has an extended portion extended from an outer edge of the predefined surface on which a non-sewn area without the specified thread member is formed.

DETAILED DESCRIPTION OF THE INVENTION

The preferred embodiments for implementing the present invention will be described referring to figures below.

Figure 1:
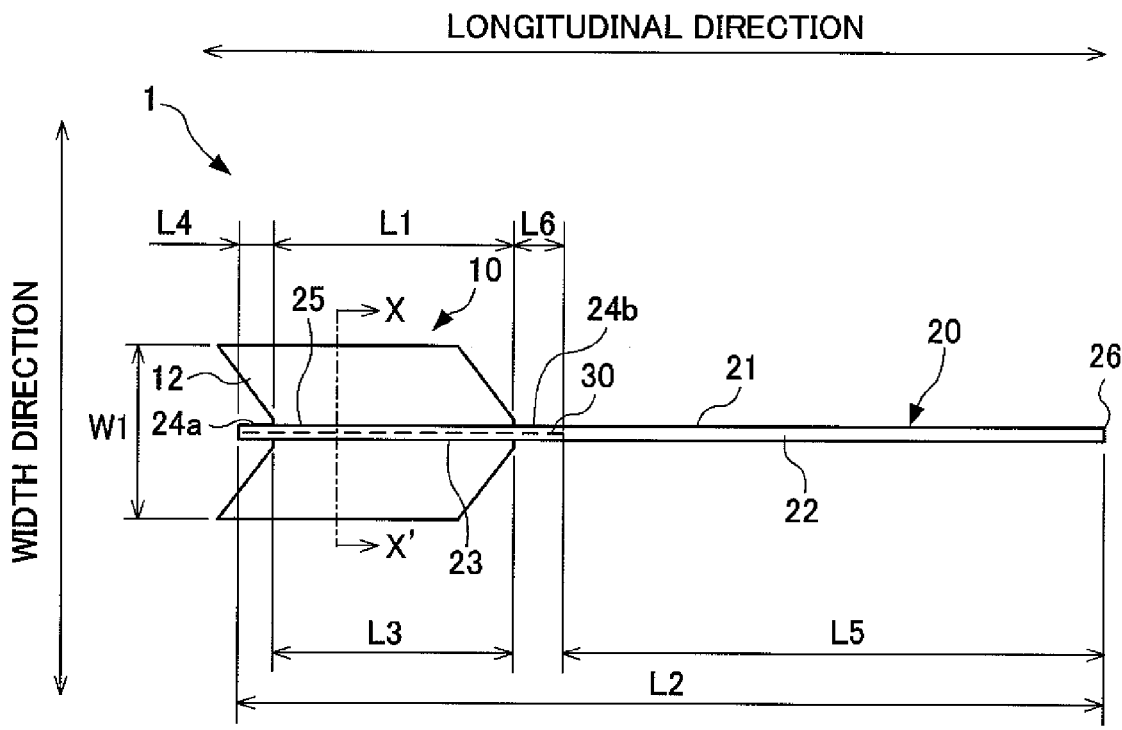
FIG. 1 shows a plan view of the sheet-like structure of Example 1.
Figure 2:
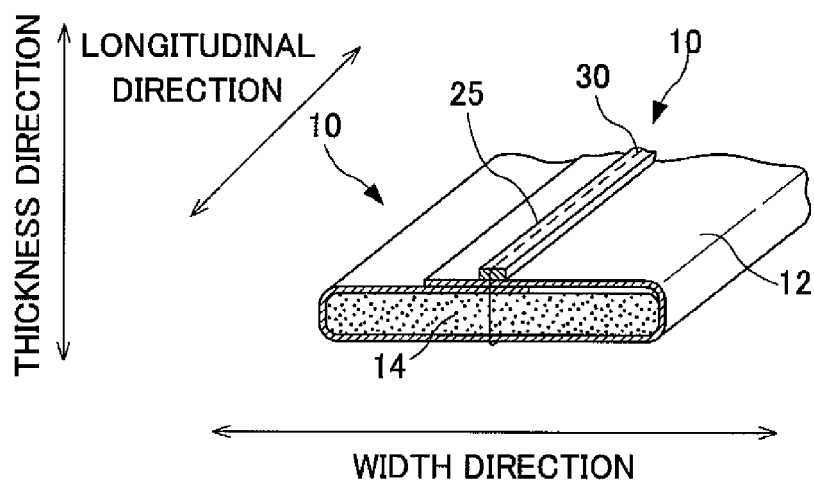
FIG. 2 shows a cross section of X-X' line in FIG. 1.
Figure 3:
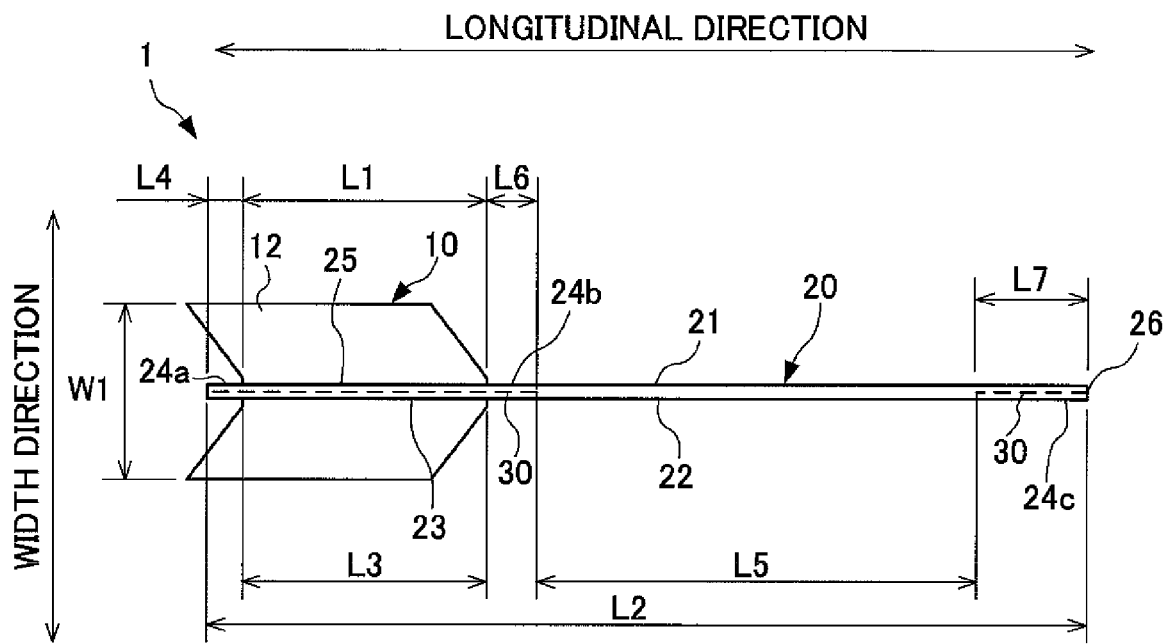
FIG. 3 shows a plan view of a sheet-like structure of Example 2.
Figure 4:
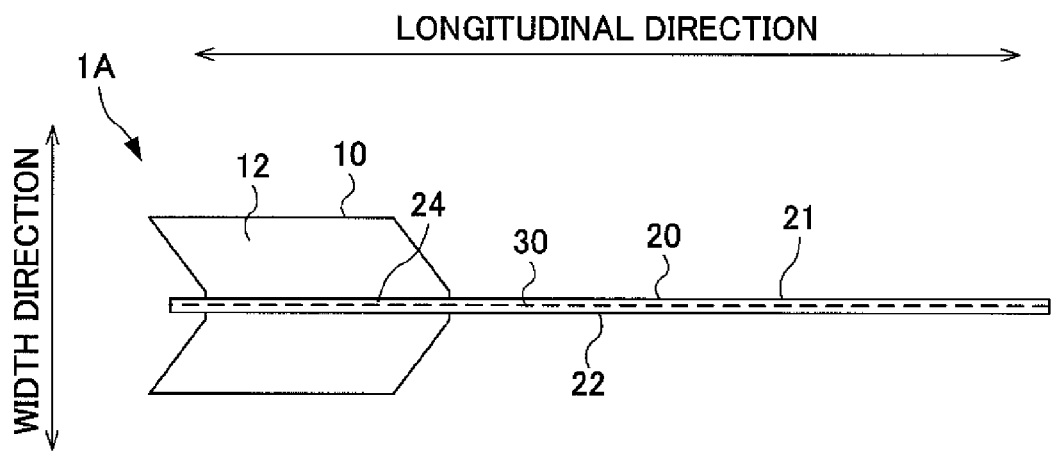
FIG. 4 shows a plan view of a conventional sheet-like structure.
Figure 5:
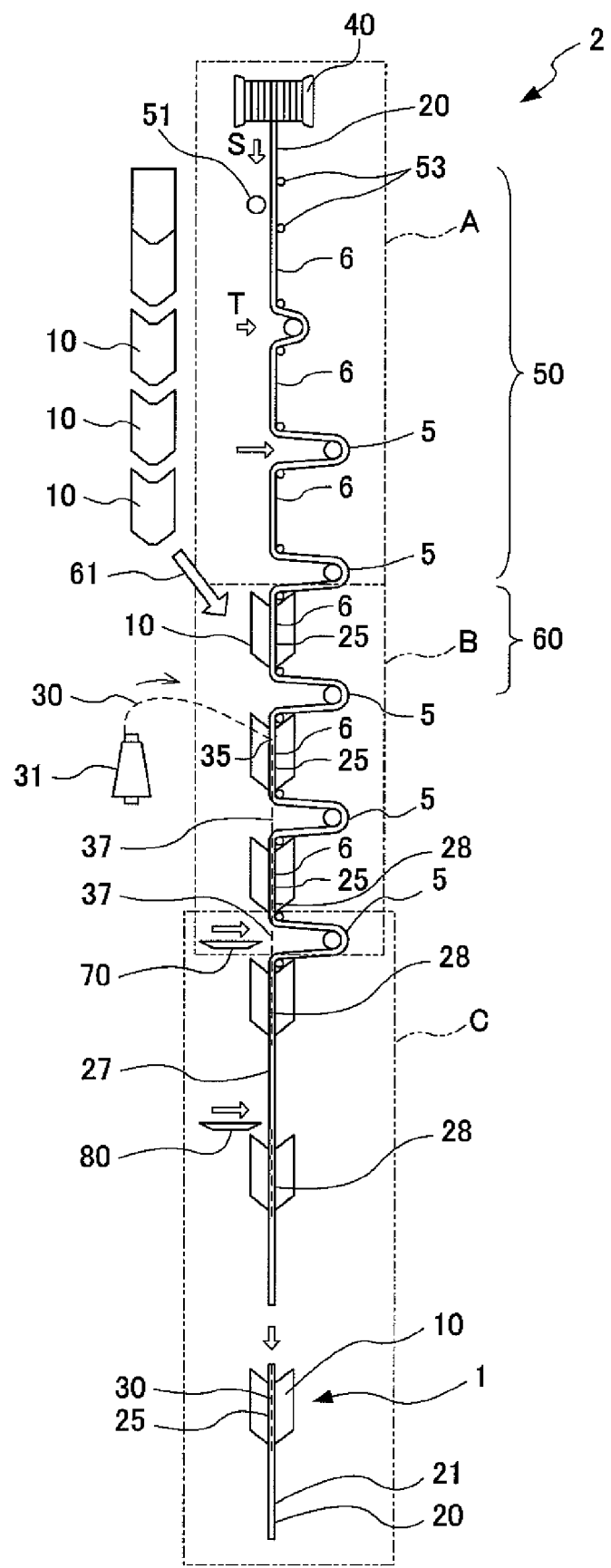
FIG. 5 shows a view describing a manufacturing system in the first embodiment of the present invention.
Figure 6:
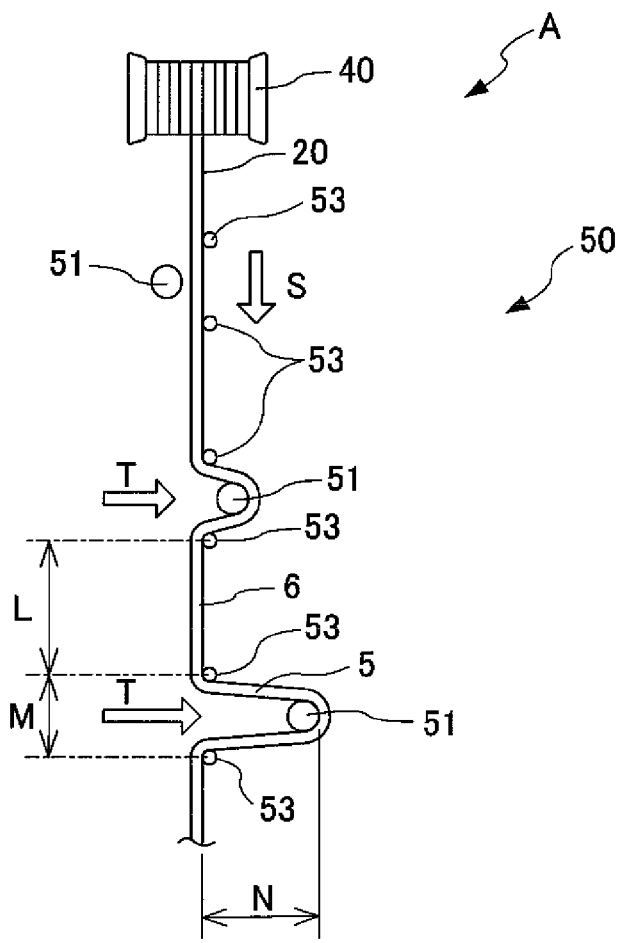
FIG. 6 shows an enlarged view of area A in FIG. 5.
Figure 7:
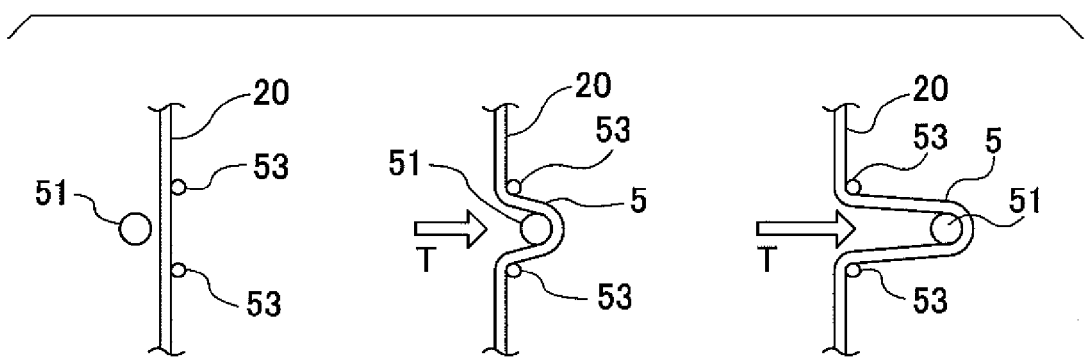
FIG. 7 shows a view describing a step of forming a loosened portion in FIG. 6.
Figure 8:
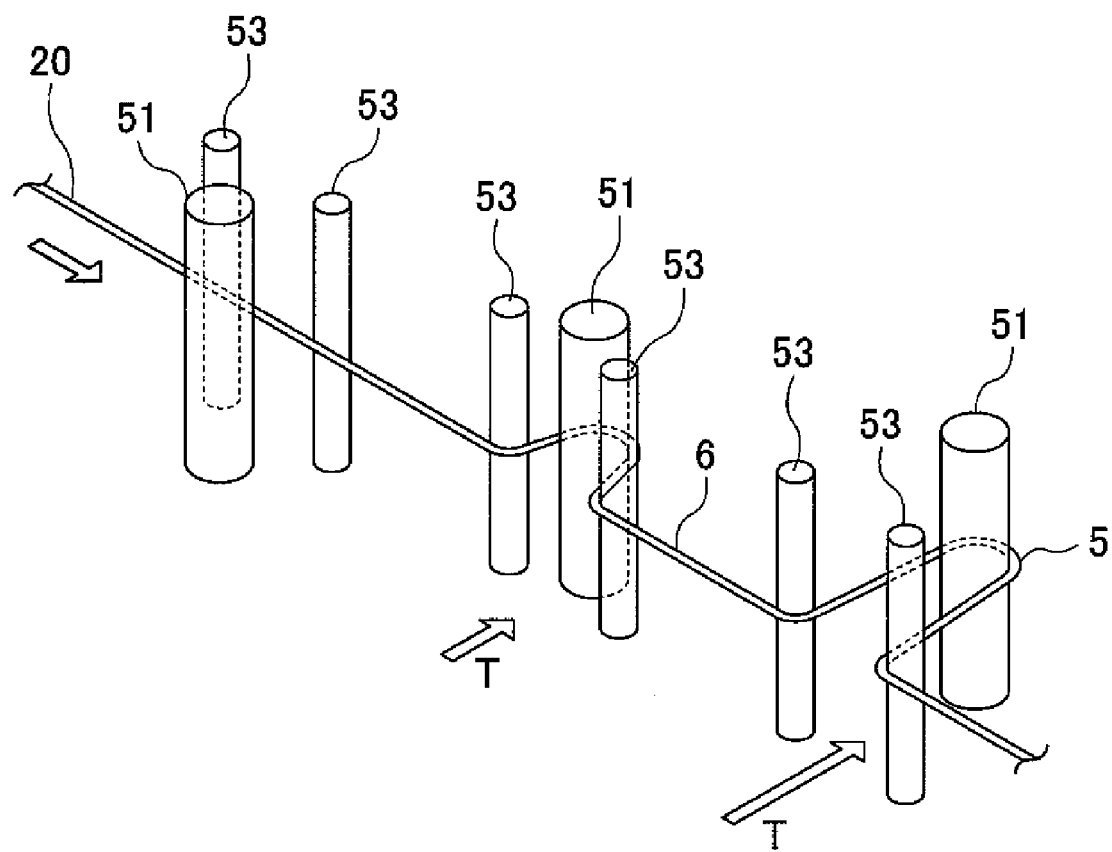
FIG. 8 shows a perspective view of area A shown in FIG. 6.
Figure 9:
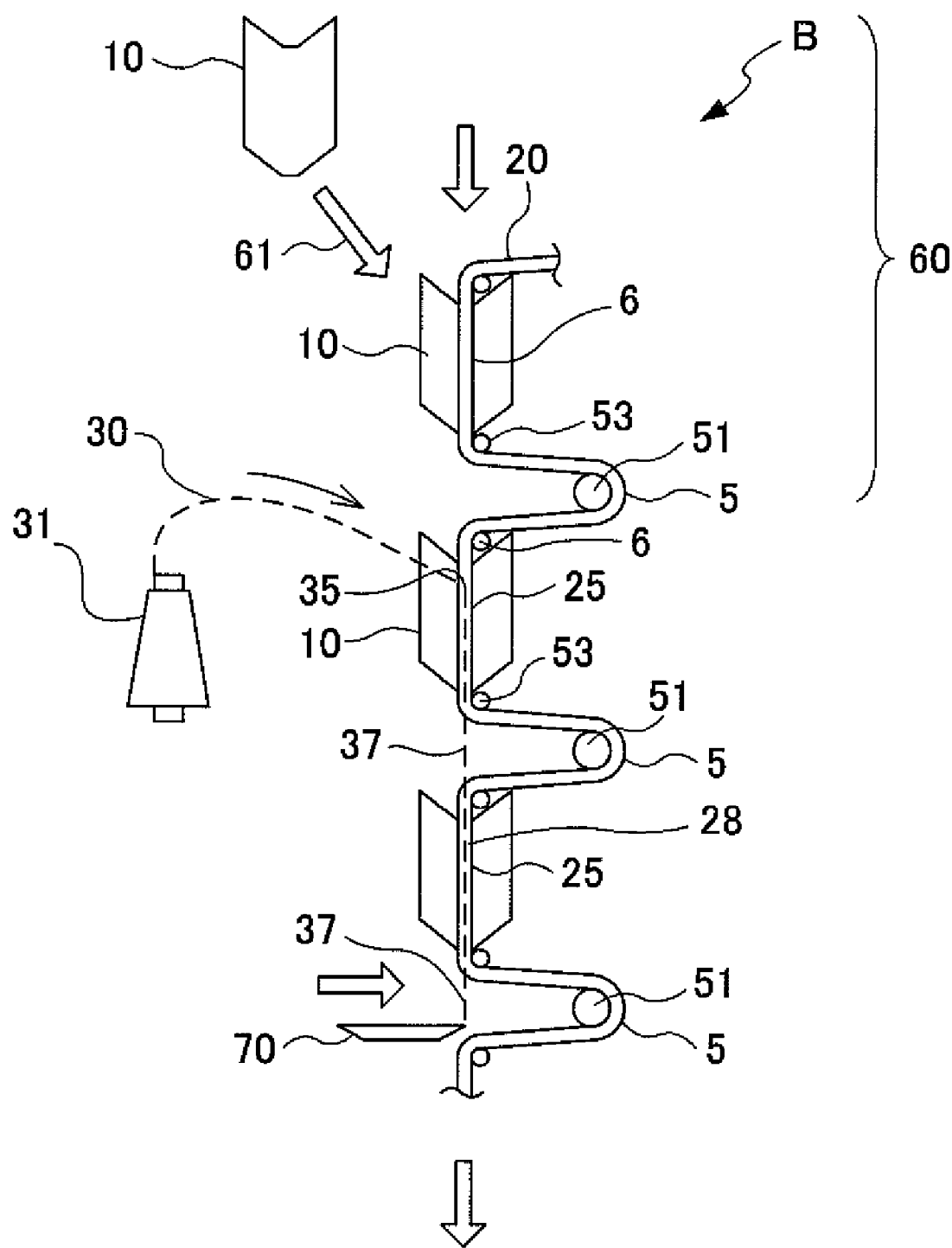
FIG. 9 shows an enlarged view of area B in FIG. 5.
Figure 10:
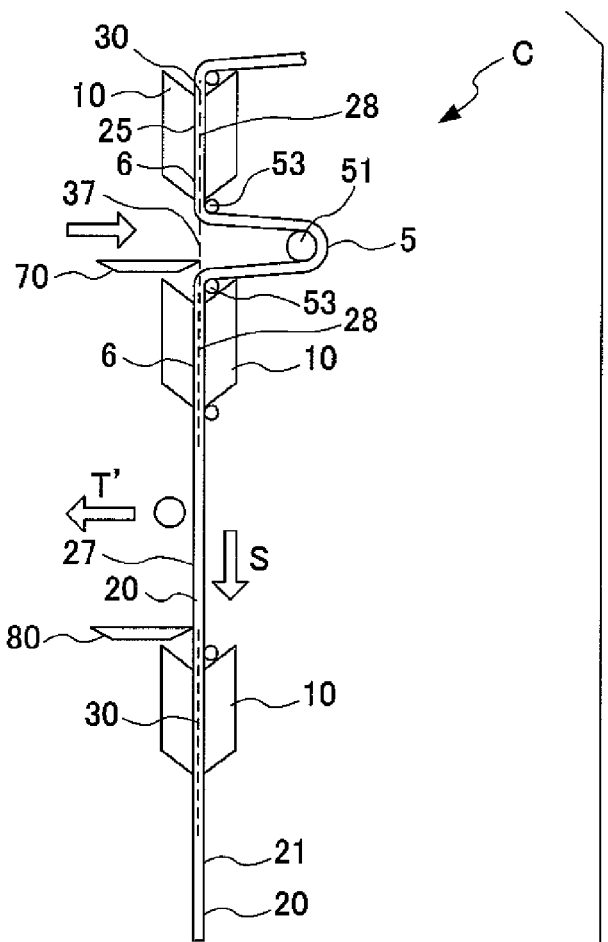
FIG. 10 shows an enlarged view of area C in FIG. 5.
Figure 10:
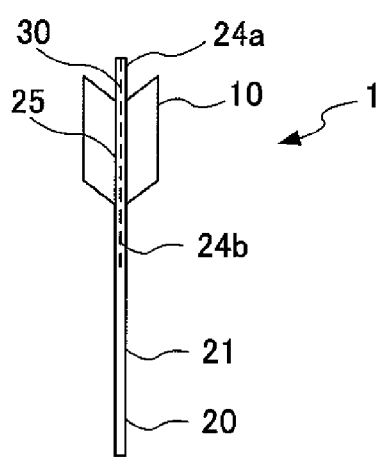
Figure 11:
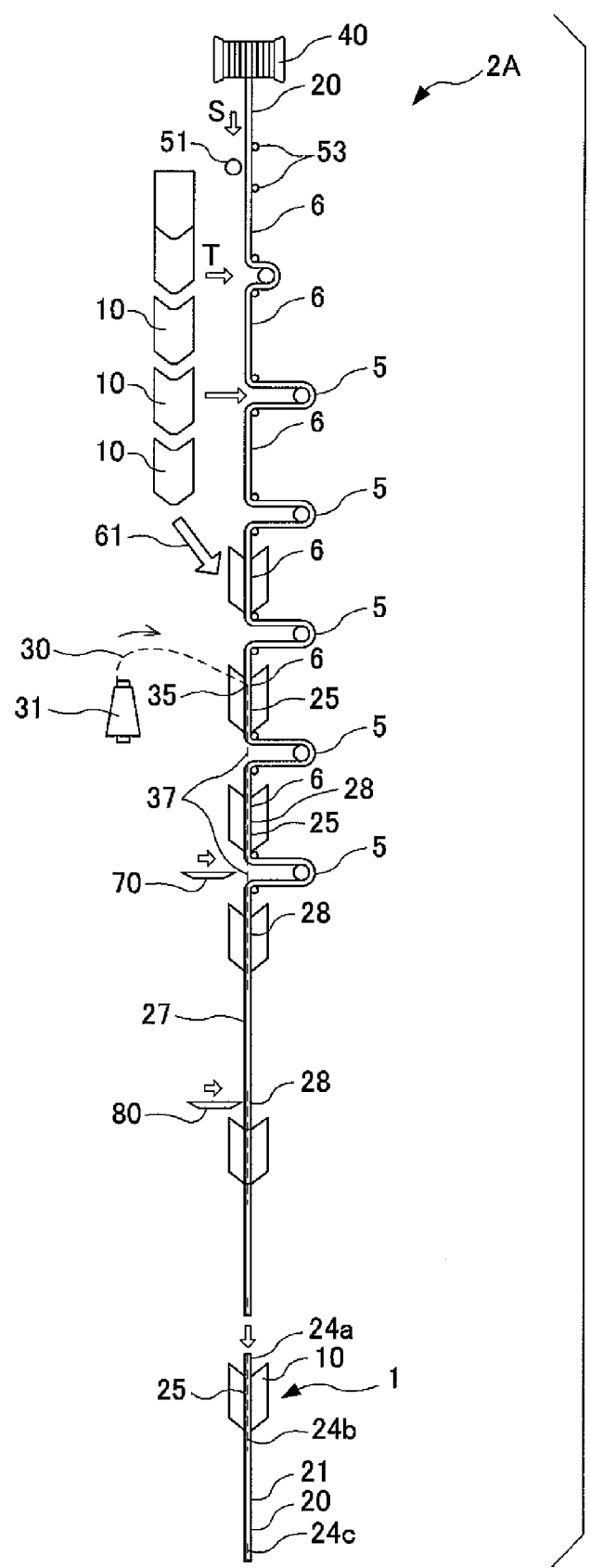
FIG. 11 shows a view describing a manufacturing system in the second embodiment of the present invention.
Figure 12:
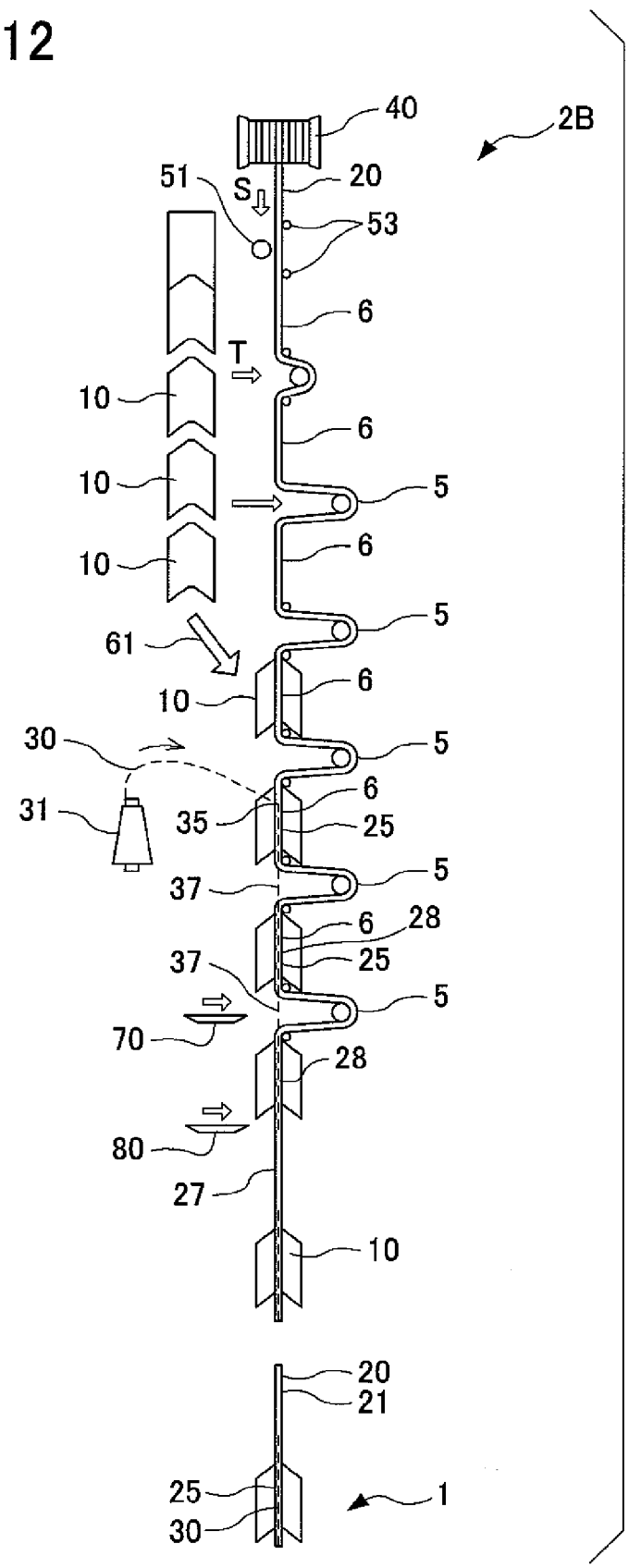
FIG. 12 shows a view describing a manufacturing system in the third embodiment of the present invention.
Figure 13:
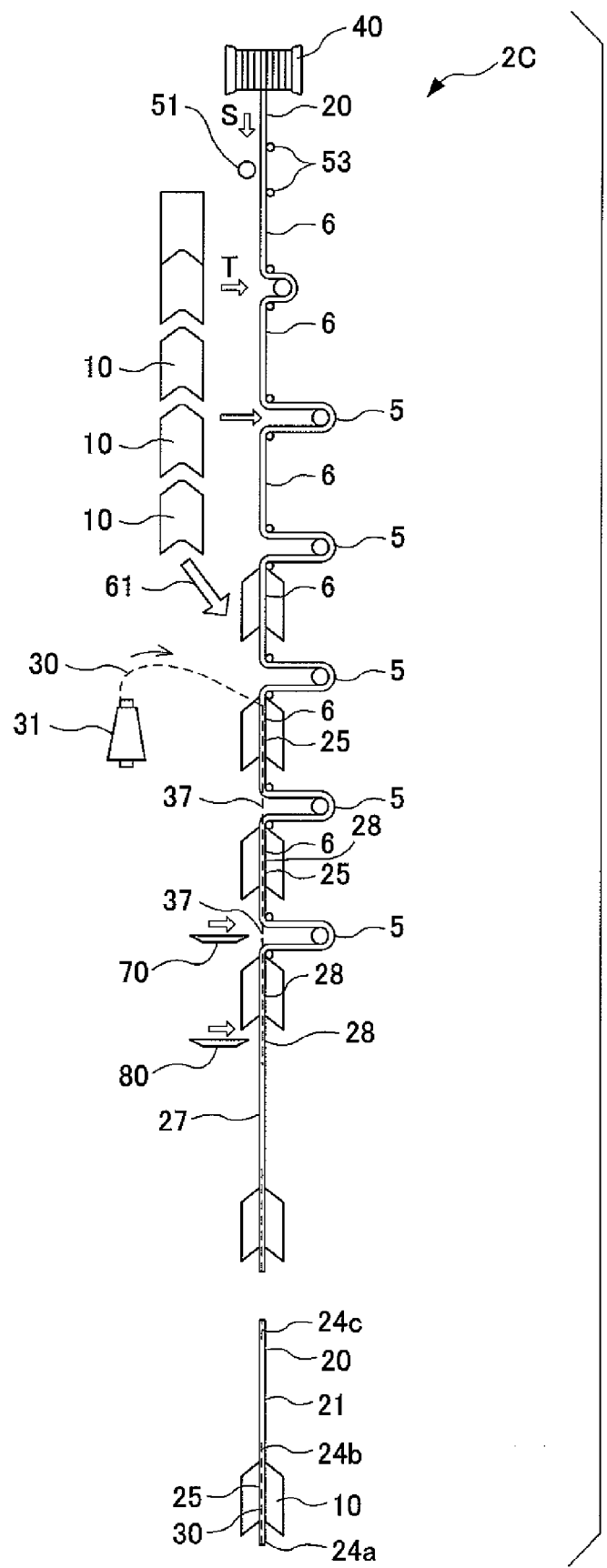
FIG. 13 shows a view describing a manufacturing system in the fourth embodiment of the present invention.

FIG. 1 shows a plan view of the sheet-like structure of Example 1. FIG. 2 shows a cross section of X-X' line in FIG. 1. FIG. 3 shows a plan view of a sheet-like structure of Example 2. FIG. 4 shows a plan view of a conventional sheet-like structure. FIG. 5 shows a view describing a manufacturing system in the first embodiment of the present invention. FIG. 6 shows an enlarged view of area A in FIG. 5. FIG. 7 shows a view describing a step of forming a loosened portion in FIG. 6. FIG. 8 shows a perspective view of area A shown in FIG. 6. FIG. 9 shows an enlarged view of area B in FIG. 5. FIG. 10 shows an enlarged view of area C in FIG. 5. FIG. 11 shows a view describing a manufacturing system in the second embodiment of the present invention. FIG. 12 shows a view describing a manufacturing system in the third embodiment of the present invention. FIG. 13 shows a view describing a manufacturing system in the fourth embodiment of the present invention.

The manufacturing system of sheet-like structures according to the present invention will be described referring to FIGS. 1 to 13.

(1.1) Whole System

The whole composition of the manufacturing system of the present invention will be described through sheet-like structures and a manufacturing system of the first embodiment shown in FIGS. 1 to 10.

(1.1.1) Sheet-Like Structure

The manufacturing target of the manufacturing system of the present invention is a sheet-like structure comprising a sheet-like member, and a cord member, which is sewn onto a predefined surface of the sheet member with a specified thread member, which has an extended portion extending from an outer edge of the predefined surface, and on which a non-sewn area, without the specified thread member, is formed. For example, as shown in FIGS. 1 to 3, a sheet-like structure 1 of the first embodiment comprises an absorbing member 10 with a planar feather-like form as a sheet-like member, and a cord member 20, which is sewn onto a predefined surface of the absorbing member 10 with a specified thread member 30, and has an extended portion 21 extending from an outer edge of the predefined surface, on which non-sewn area 22 without the thread member 30 is formed. The sheet-like structure 1 according to the present invention can be used as an absorbing body for tampons.

Specifically, the sheet-like structure 1 comprises the absorbing member 10 with a planar feather-like form, and a cord member 20 in which a part thereof is arranged in contact with a predefined surface of the absorbing member 10 so that it is extended in the longitudinal direction in an substantially center of the width direction of the absorbing member 10 and sewn with the thread member 30 as shown in FIGS. 1 to 3. The cord member 20, which is longer than the length of the absorbing member 10 in the longitudinal direction, has the extended portion 21 extending from an outer edge of the absorbing member 10 in the longitudinal direction. When the sheet-like structure 1 is used as an absorbing body for tampons, the absorbing member 10 is formed into a substantially cylindrical form by compression, to be placed in an applicator (not shown).

As shown in FIG. 2, the absorbing member 10 as a sheet-like member has an absorbing layer 14 comprising absorbent fiber material, and a surface material 12 with liquid permeability which covers the absorbing layer 14 so as to wrap the absorbing layer 14 in the width direction. The absorbing member 10 as a sheet-like member of the embodiment may have a dimension of total length in the longitudinal direction of 30 mm to 90 mm and total length in the width direction of 30 mm to 70 mm, for example. The absorbing member 10 is acceptable as long as it is in the sheet-like form, and the planar form is not limited. Examples of the planar form of the absorbing member 10 include square, rectangle and oval shape. It is preferable to lengthen the length of the absorbing member 10 as an absorbing body for tampons because it enables reduction of leakage due to the lengthened contact and absorbing length (the length of an area where the absorbing body and the inner wall of vagina come in contact with each other). However, this may be a cause of unpleasant sensation during use and it is more preferable for the absorbing member 10 to be in a feather-like form as shown in FIGS. 1 and 3. More specifically, it is favorable because the amount and density of the fiber can be decreased at both front and back edges of the absorbing body for tampons after forming by compression, while the absorbing member 10 is lengthened to prevent occurrence of unpleasant sensations. In addition, resistance to removal is reduced making it easier to be pulled off after use.

Examples of the absorbent fiber material used for the absorbing layer 14 include hydrophilic fibers such as cotton, rayon and synthetic fiber. Single or multiple fiber webs, nonwoven or woven fabrics, preferably having a weight of 150 $g/m^2$ to 1,500 $g/m^2$ and a thickness of substantially 0.1 mm to 0.9 mm are lapped over another to form an absorbing layer having a thickness of 1.0 mm to 15 mm and preferably having a thickness of 2.0 mm to 10 mm is used as the absorbing layer 14. There are fiber webs and nonwoven fabrics shaped by card webbing, air-laying method, wetlaid method and the like, on a base such as a synthetic fiber sheet. Hydrophobic fibers or hydrophobic fibers provided with a hydrophilic property may also be comprised in the absorbing layer 14 with the hydrophilic fibers. In addition, compounds having a water absorbing property, such as polymers with a high water absorbing property, may be comprised in the absorbing layer 14.

The surface material 12 with liquid permeability is made of nonwoven fabrics formed by hydrophobic fibers or mesh films, to which mesh treatment has been performed. The type of nonwoven fabrics used for the surface material 12 is not particularly limited and examples include spunbond nonwoven fabrics, spunlace nonwoven fabrics and thermal bond nonwoven fabrics. The hydrophobic fiber which makes up the nonwoven fabrics is not particularly limited and examples include fibers of polyester, polypropylene and polyethylene. The weight of the nonwoven fabrics is preferably 8 $g/m^2$ to 40 $g/m^2$. The mesh film is preferably a polyolefin film such as polypropylene or polyethylene.

The cord member 20 is arranged in contact with a predefined surface of the absorbing member 10 so that it is extended in the longitudinal direction in the substantially center of the width direction of the absorbing member 10, and comprises a sewn area 25 sewn with the thread member 30.

The cord member 20, which is longer than the length of the absorbing member 10 in the longitudinal direction, has the extended portion 21 extended from an outer edge of the absorbing member 10 in the longitudinal direction.

Strings made of natural or synthetic fibers, resin-made cords, threads of more than predetermined diameter and composite yarns formed by twisting number of above threads can be used as the cord member 20. Composite yarns formed by twisting plural cotton threads or single threads such as polyester threads can be used when making an absorbing body for tampons, for example. The cord member 20 is preferably water repellent finished by attaching paraffin, for example, in order to prevent contamination from outside of the body, such as urine, from being drawn into the cord member during use. The length of the cord member 20 is preferably 110 mm to 250 mm when the length of the absorbing member is 30 mm to 90 mm, for example.

Sewn areas 24a, 25, and 24b, and non-sewn area 22 are formed along a cord member 20 of the sheet-like structure 1 in Example 1 as shown in FIG. 1. Sewn areas 24a, 25 and 24b, non-sewn area 22, and sewn area 24c are formed along a cord member 20 of the sheet-like structure 1 in Example 2 as shown in FIG. 3. The non-sewn area 22 and the sewn area 24c are formed on an extended portion 21. The sewn areas 24a, 24b, 24c, and 25 contain a thread member 30 and the non-sewn area 22 does not contain the thread member 30.

The sewn area 25 is formed on an entire surface or a part of a contact portion 23 where the cord member 20 is in contact with the absorbing member 10, which is a sheet-like member. The sewn area 25 is formed on the entire surface of the contact portion 23 in the first to fifth embodiments described below.

The non-sewn area 22 which does not comprise the thread member 30 is formed on the extended portion 21 as described above. That is, the thread member 30 forming the sewn area 25 is not continued to a free end 26 of the extended portion 21.

Specifically, the sewn area 24b of a predefined length is formed with the same thread member 30 forming the sewn area 25 on an extended portion 21 in the sheet-like structure 1 of Example 1 sequentially from the sewn area 25 while the non-sewn area 22 not sewn with the thread member 30 is formed from an edge opposite of the sewn area 25 side of the sewn area 24b to the free end 26 of the extended portion 21.

As shown in FIG. 3, the sewn area 24b is formed sequentially from the sewn area 25 on the extended portion 21 of the sheet-like structure 1 in Example 2, similar to Example 1. The sewn area 24c is formed with a thread member 30 on the free end 26 of the extended portion 21 and its vicinity. The non-sewn area 22, which is not sewn with the thread member 30, is formed between the sewn areas 24b and 24c. That is, the sewn areas 24b and 24c are separated across the non-sewn area 22. When the cord member is cut at a specified position of a sewn area 28 formed in a predefined area as described in the manufacturing system and the method for manufacturing sheet-like structure 1 below, sewn areas 24a and 24c are separated to one side and the other side.

The cord member 20 and the absorbing member 10 which is a sheet-like member are connected and combined by sewing the sewn area 25. The sewn area 24c works to prevent unraveling of the multiple threads when the cord member 20 is formed by twisting multiple threads, for example.

The thread member 30 is acceptable as long as a member is made of materials which can sew the absorbing member 10 as a sheet member and the cord member 20 together and it is finer than a predetermined diameter. Examples include threads formed by natural materials, threads of synthesized fibers and fine wires. For example, a thread formed by twisting a number of single threads such as cotton threads can be used for the sheet-like structure 1 of Examples 1 and 2. These threads are water repellent finished by attaching paraffin, etc. as necessary.

As shown in FIG. 4, a sewn area 24 is formed on an entire length of the cord member 20 of a conventional sheet-like structure 1A. At the same time, an entire length of the sewn areas 24a, 24b, and 25 relative to the entire length L2 of the cord member 20 of the sheet-like structure 1 in Example 1 may be 20% to 90%. The entire length of the sewn areas 24a, 24b, 24c and 25 relative to the entire length L2 of the cord member 20 of the sheet-like structure 1 in Example 2 may be 20% to 90%.

That is, the sheet-like structure 1 of Example 1 and Example 2 can prevent the thread member 30 from coming off while also preventing liquid leakage because the thread member 30 forming the sewn area 25 is not continued to the free end 26. Furthermore, used amount of the thread member 30 used for the sheet-like structure 1 can be controlled. For example, the used amount of the thread member 30 can be reduced to substantially 20% to 90% as compared to the conventional sheet-like structure 1A as shown in FIG. 4.

This is advantageous in terms of cost. That is, cost of the thread member 30 is reduced. Moreover, the weight of the sheet-like structure 1 can be reduced because used amount of the thread member 30 is reduced. Furthermore, this is significantly advantageous for the manufacturing process because this reduces sewing considerably.

Specifically, the time it takes for sewing can be shortened, thereby shortening the manufacturing time and improving the productivity considerably. For example, productivity can be improved up to substantially 110% to 400% relative to the productivity of the conventional sheet-like structure 1A as shown in FIG. 4.

Moreover, the time taken for sewing or other steps can be lengthened by the time shortened, and the steps are performed more thoroughly, thereby the quality of the sheet-like structures can be improved.

Furthermore, when a sheet-like structure is manufactured by the manufacturing system 2, described below, the manufacturing line can be shortened more than conventional manufacturing line.

(1.1.2) Outline of Manufacturing System

The manufacturing system (apparatus) 2 of the sheet-like structure 1 in the first embodiment is equipped with a cord member reeling-out unit 40 which is a cord member reeling-out apparatus, a loosened portion forming unit 50 which is a loosened portion forming apparatus, an arranging unit 60 which is an arranging apparatus, a sewing machine unit 35 which is a sewing apparatus, a thread member cutter 70 which is a thread member cutting apparatus and a cord member cutter 80 which is a cord member cutting apparatus as shown in FIG. 5.

(1.2) Cord Member Reeling-Out Apparatus

The cord member reeling-out unit 40 which is a cord member reeling-out apparatus reels out the cord member 20 in a specified direction. The cord member 20 is placed in the cord member reeling-out unit 40, rolled up in a substantially cylindrical form. The cord member 20 can be reeled out by rotating the cylinder around its cylindrical axis. The length of the cord member 20 reeled out from the cord member reeling-out unit 40 can be adjusted by controlling the rotating speed of the cylinder by means of variable speed motors, etc.

(1.3) Loosened Portion Forming Apparatus

The loosened portion forming unit 50 which is a loosened portion forming apparatus forms plural loosened portions 5, which are substantially U-shaped and extend in a direction T perpendicular to a specified direction S, on a cord member reeled out from a cord member reeling-out unit 40 in the specified direction S. Plural linear portions 6 in a substantially linear form, connecting each of the plural loosened portions 5, are then formed.

The loosened portion forming unit 50 will be further explained referring to FIGS. 6 to 8. As shown in FIG. 6, the cord member 20 reeled out from the cord member reeling-out unit 40 is placed between a movable guide 51 and a fixed guide 53, as shown in FIG. 6. The movable guide 51 and the fixed guide 53 in the initial state are placed on one side and the other side across the cord member 20.

The plural fixed guides 53 are placed substantially linearly along the direction S. The plural fixed guides 53 are placed so that a distance L and a distance M are formed alternately. The distance L is set, based on the length of the linear portion 6, the sewn area 25, or the sewn area 24c, and the distance M is set based on the diameter of the movable guide 51 and the length of the loosened portion 5.

The movable guides 51 are placed at positions not overlapping with the fixed guides 53 in the direction S. Specifically, the movable guides 51 are placed between a specified fixed guide 53 and the fixed guides 53 which lie adjacent to the specified fixed guide 53.

The movable guides 51 move in a direction T perpendicular to the direction S to form the loosened portions 5, which are substantially U-shaped and extend in the direction T, on the cord member 20. The length L5 of the loosened portion 5 in FIGS. 1 and 3 are adjusted depending on the distances M and N or diameter of the movable guide 51 in FIG. 6.

As shown in FIG. 5, the loosened portion forming unit 50 forms plural linear portions 6 formed between a specified fixed guide 53 and its adjacent fixed guides 53. The plural linear portions 6 are placed substantially linearly along the direction S. The sewn areas 25 are formed on contact portions 23 where the linear portions 6 come in contact with the absorbing member 10 by sewing each of the linear portions 6 along the straight line by means of the sewing machine unit 35 which is a sewing apparatus. The sewn areas 24a, 24b, and 24c in FIGS. 1 and 3 can also be formed continuously by sewing the entire length of the linear portion 6.

The sewn area 24c can be formed by making the distance L in FIG. 6 longer than the length L1 of the absorbing member 10 which is a sheet member in FIG. 3. In other words, a sewn area 28 of a predefined length is formed by sewing the portion of the cord member 20 extended from the absorbing member 10. The sewn area 24a in a specified sheet-like structure 1 and the sewn area 24c on a free end 26 of the extended portion 21 in the sheet-like structure 1, which lies adjacent to the specified sheet-like structure 1, can be formed by cutting a specified portion of the sewn area 28 of a predefined length by means of a cord member cutter 80 which is a cord member cutting apparatus.

(1.4) Arranging Apparatus

The arranging unit 60 which is an arranging apparatus arranges each of the plural absorbing members 10 on each of the plural linear portions 6 formed by the loosened portion forming unit 50 which is a loosened portion forming apparatus so that the absorbing members 10 come in contact with the linear portions 6. Specifically, the plural absorbing members 10, as sheet members arranged sequentially, are moved in a direction of an arrow 61 by means of conveyers (not shown), to be arranged on lower sides of the linear portions 6 formed between adjacent fixed guides 53 so that the absorbing members 10 come in contact with the linear portions 6 as shown in FIG. 5.

(1.5) Sewing Apparatus

The sewing machine unit 35 which is a sewing apparatus sews each of the plural absorbing members 10 as sheet members placed by the arranging unit 60, and each of the plural linear portions 6 placed so as to come in contact with the absorbing members 10, with a thread member 30. Specifically, the plural absorbing members 10 placed so as to come in contact with each of the plural linear portions 6 by the arranging unit 60 are sewn from upper sides of the plural linear portions 6 formed by the loosened portion forming unit 50 and arranged substantially linearly, as shown in FIGS. 5 and 9.

Specifically, the plural linear portions 6 are sent forth continuously along the straight line formed by the plural linear portions 6 to a sewing position in the fixed sewing unit 35. Sewing is performed continuously by the sewing unit 35 with the thread member 30. In this way, sewn areas 25 are formed on the contact portions 23 where the absorbing members 10 and the linear portions 6 come in contact with each other, and sewn areas 24a, 24b and 24c are formed on the cord members 20 as shown in FIGS. 1 and 3. Furthermore, thread connecting portions 37, which are parts of the thread member 30 formed so as to connect a specified absorbing member 10 and the absorbing members 10 which lie adjacent to the specified absorbing member 10, are formed.

(1.6) Thread Member Cutting Apparatus

The thread member cutter 70 which is a thread member cutting apparatus cuts thread connecting portions 37 which are parts of the thread member 30 formed so as to connect adjacent absorbing members 10 on which each of the plural linear portions 6 are sewn by the sewing machine unit 35 which is a sewing apparatus.

Various cutter members may be used as thread member cutters 70. For example, roll cutter members (not shown) may be used. The distance between each absorbing member 10 can be adjusted by cutting the thread member 30 making up the thread connecting portions 37 by means of the thread member cutter 70, and extending the cord member 20 forming the cord connecting portions 27 substantially linearly becomes possible.

(1.7) Cord Member Cutting Apparatus

A cord member cutter 80 which is a cord member cutting apparatus cuts, at a specified position, the cord connecting portions 27, which are parts of the cord member 20 formed so as to connect a specified absorbing member 10 of the plural absorbing members 10 and the absorbing members 10 which lie adjacent to the specified absorbing member 10. The distance between the specified absorbing member 10 and its adjacent absorbing member 10 is lengthened, while the cord connecting portion 27 is extended substantially linearly because the thread member 30 which makes up the thread connecting portions 37 is already cut by the thread member cutter 70, thereby enabling the cord member 20 to be cut while the cord connecting portions 27 are extended substantially linearly.

Specifically, the movable guide 51 is moved in a direction T' after the thread member 30, which makes up the thread connecting portions 37, is cut by the thread member cutter 70, as shown in FIG. 10. Furthermore, the loosened portions 5 can be extended substantially linearly by increasing the moving velocity of the fixed guide 53 in the direction S. The length of the extended portions 21, etc. can be suitably adjusted by extending the loosened portions 5, and preferably extending the sequential linear portions 6 substantially linearly as described above.

(1.8) Sheet Member Forming Apparatus

The absorbing member 10 which is a sheet member in the first embodiment is a sheet-like absorbing member 10 containing a specified absorbing layer 14 with liquid absorbability coated with a surface material 12 in a thin film form. The manufacturing system of sheet-like structures 2 in the first embodiment may be equipped with a sheet member forming apparatus by which the absorbing layer 14 (not shown) is coated with the surface material 12 of thin film form. Examples of the sheet member forming apparatus include a specific apparatus by which the absorbing layer 14 with a prescribed form is coated so as to be wrapped with the surface material 12 having a width longer than the outer circumference in a short side direction of the absorbing layer 14.

Furthermore, plural absorbing member 10 can be formed by combining an apparatus by which the absorbing layer 14, with an substantially belt-like form, is coated so as to be wrapped with the surface material 12, having a width longer than the outer circumference in a short side direction of the absorbing layer 14, an apparatus such as specific emboss rolls which artificially combine the surface material 12 and the absorbing layer 14 to be formed into an substantially sheet form by heating and pressurizing, while the surface of the absorbing layer 14 is coated with the surface material 12, and an apparatus by which the belt-like absorbing member which is a material of the absorbing member 10 is cut into prescribed forms.

(1.9) Other Items

When the sheet-like structure 1 in the first embodiment is used which is an absorbing medium for tampons, a compressing apparatus (not shown) by which the absorbing member 10 is compressed to be inserted into a prescribed applicator, may be further included.

(2) Second Embodiment

As shown in FIG. 11, a manufacturing system for sheet-like structures 2A in the second embodiment is a system by which a sheet-like structure 1 as shown in FIG. 3 is manufactured. Specifically, the sheet-like structure 1 is a sheet-like structure in which a sewn area 24c is formed on a free end 26 of the extended portion 21.

Although the manufacturing system of sheet-like structures 2A in the second embodiment is similar to the manufacturing system of sheet-like structures 2 in the first embodiment, it differs in the length L of the linear portion 6. Specifically, the length L of the linear portions 6 of the manufacturing system 2A in the second embodiment is set longer than the length of the linear portions 6 of the manufacturing system 2 in the first embodiment.

In other words, a sewn area 28 is formed on one side of the absorbing member 10 in the second embodiment because the length L of the linear portion 6 is set longer than the length L1 of the absorbing member 10 by a prescribed length.

A sheet-like structure 1 in which the sewn area 24c is formed on the free end 26 side of the extended portion 21 by cutting a specified portion of the sewn area 28 in the cord connecting portion 27, formed so as to connect a specified absorbing member 10 and its adjacent absorbing members 10. Meanwhile, the descriptions in the first embodiment can be applied to other apparatuses in the second embodiment.

(3) Third Embodiment

As shown in FIG. 12, a manufacturing system of sheet-like structures 2B in the third embodiment is a system by which the sheet-like structure 1 as shown in FIG. 1 is manufactured.

Although the manufacturing system of sheet-like structures 2B in the third embodiment is similar to the manufacturing system of sheet-like structures 2 in the first embodiment, it differs in the direction of the absorbing member 10. Specifically, the absorbing member 10 of the manufacturing system 2 in the first embodiment is manufactured while the convex side of the feather-like form is turned to the direction S, which is a traveling direction, whereas the absorbing member 10 of the manufacturing system 2B in the third embodiment is manufactured while the convex side of the feather-like form is turned to a direction opposite of the direction S, which is a traveling direction.

In addition, positions at which the cord connecting portions 27 formed so as to connect a specified absorbing member 10 and its adjacent absorbing members 10 are cut by the cord member cutter 80, which is a cord member cutting apparatus, differ between the first and the third embodiment. In the first embodiment, a vicinity of an outer edge of the absorbing member 10 in the direction opposite to the direction S is cut, whereas a vicinity of an outer edge of the absorbing member 10 in the direction S is cut in the third embodiment. Meanwhile, the descriptions in the first embodiment can be applied to other apparatuses in the third embodiment.

(4) Fourth Embodiment

As shown in FIG. 13, a manufacturing system of sheet-like structures 2C in the fourth embodiment is a system in which a sheet-like structure 1 as shown in FIG. 3 is manufactured. The sheet-like structure 1 is a sheet-like structure in which a sewn area 24c is formed on a free end 26 of the extended portion 21.

Although the manufacturing system of sheet-like structures 2C in the fourth embodiment is similar to the manufacturing system of sheet-like structures 2A in the second embodiment, it differs in the direction of the absorbing member 10. Specifically, the absorbing member 10 of the manufacturing system 2A in the second embodiment is manufactured while the convex side of the feather-like form is turned to the direction S, which is a traveling direction, whereas the absorbing member 10 of the manufacturing system 2C in the fourth embodiment is manufactured while the convex side of the feather-like form is turned to a direction opposite of the direction S, which is a traveling direction.

In addition, positions at which the cord connecting portions 27, formed so as to connect a specified absorbing member 10 and its adjacent absorbing members 10, are cut by the cord member cutter 80, which is cord member cutting apparatus differ between the second and the fourth embodiment. In the second embodiment, vicinity of an outer edge of the absorbing member 10 in the direction opposite to the direction S is cut whereas vicinity of an outer edge of the absorbing member 10 in the direction S is cut in the fourth embodiment. Meanwhile, the descriptions in the first embodiment can be applied to other apparatuses in the fourth embodiment.

(5) Method for Manufacturing

The method for manufacturing sheet-like structures of the present invention contains a sheet member with a prescribed form, a cord member which is sewn onto a predefined surface of the sheet member with a specified thread member, and having an extended portion extended from an outer edge of the predefined surface on which a non-sewn area without the specified thread member is formed, forming a loosened portion in which plural loosened portions, which are substantially U-shaped and extended in a direction different to a specified direction, are formed on a cord member reeled out in the specified direction, and plural linear portions, which connect each of the plural loosened portions respectively, are formed substantially linearly, arranging in which each of the plural sheet members are arranged so as to be in contact with each of the plural linear portions formed in the forming the loosened portion, sewing in which each of the plural linear portions which come in contact with the plural sheet members are sewn with a thread member on each of the plural sheet members arranged in the arranging, cutting a thread member in which thread connecting portions, which are parts of the thread member formed so as to connect a specified sheet member of the plural sheet members on which each of the plural linear portion are sewn in the sewing and other sheet members which lie adjacent to the specified sheet member, are cut, and cutting a cord member in which cord connecting portions, which are parts of the cord member formed so as to connect a specified sheet member of the plural sheet members and other sheet members which lie adjacent to the specified sheet member, are cut at a specified position.

The manufacturing target of the method for manufacturing according to the present invention is a sheet-like structure containing a sheet member with a prescribed form and a cord member which is sewn onto a predefined surface of the sheet member with a specified thread member and having an extended portion extended from an outer edge of the predefined surface on which non-sewn area without the specified thread member is formed. The sheet member of the sheet-like structure is a substantially sheet-like member made of a material on which cord members can be sewn with a specified thread member, and examples include fabric members, rubber members, and sheet-like absorbing members which make up the above-mentioned absorbing member for tampons. The cord member sewn onto the sheet member is made of a material which can be sewn onto the sheet members, and examples include strings made of natural or synthesized fibers, resin-made cords, threads of more than specified diameter and composite yarns formed by twisting number of above threads. Moreover, the thread member is a member formed of a material which can sew the sheet member and the cord member together and is finer than a specified diameter, and examples include threads formed of natural materials, threads of synthesized fibers and fine wires.

In the step of forming the loosened portion, plural loosened portions, which are substantially U-shaped and extend in a direction different to a specified direction, are formed on a cord member reeled out in the specified direction from a thread supplying unit in which thread members are winded up, for example. Plural linear portions, which connect each of the plural loosened portions respectively, are formed substantially linearly. These loosened portions become extended portions in the sheet-like structure and the linear portions become portions sewn onto the sheet member.

In the step of arranging, each of the plural sheet members are arranged so as to be in contact with each of the plural linear portions formed in the forming the loosened portion. By arranging as above, continuous sewing is possible in the step of sewing described below.

In the step of sewing, each of the plural sheet members arranged in the step of arranging, and each of the linear portions which come in contact with each of the plural sheet members, are sewn together with a thread member. For example, sheet members and a cord member are sewn together by sewing continuously along the cord member which is in contact with the sheet members by means of a specified sewing machine while loosened portions of the cord member are not sewn. In this way, non-sewn areas can be formed on the cord member who makes up the loosened portions that will be extended portions.

The thread connecting portions, which are parts of the thread member formed so as to connect the specified sheet member of the plural sheet members, on which each of the plural linear portions are sewn in the sewing, and other sheet members which lie adjacent to the specified sheet member, are cut in the step of cutting the thread member. In addition, cord connecting portions, which are parts of the cord member formed so as to connect a specified sheet member of the plural sheet members and the sheet members which lie adjacent to the specified sheet member, are cut at a specified position in the step of cutting the cord member. The order of steps of cutting the thread member and cutting the cord member is not specified and may be performed simultaneously.

The steps of cutting the thread member and the cutting the cord member may be exemplified by cutting performed by means of specified cutter members and roll members on which a convex blade is formed on a predefined surface.

The method for manufacturing in the present invention further includes a step of reeling-out a cord member in which a cord member is reeled out in a specified direction. In this way, a thread member can be supplied continuously in the specified direction.

In the method for manufacturing in the present invention, plural linear portions are arranged alongside substantially linearly at specified intervals in the step of forming the loosened portion. In this way, sewing can be performed easily in the step of sewing.

In the method for manufacturing in the present invention, each of the plural linear portions, arranged alongside substantially linearly at specified intervals in the step of forming the loosened portion, is sewn continuously onto each of the plural sheet members along a straight line formed by the plural linear portions with a thread member in the step of sewing. This enables sewing to be performed easily in the step of sewing and allows precise sewing to be performed continuously.

In the method for manufacturing in the present invention, the step of cutting the cord member contains a step of extending the cord connecting portion substantially linearly. This enables the cord member, which makes up the cord connecting portions, to be easily cut, and also enables the lengths of the extended portions formed by the cord connecting portions to be made constant. In addition, the length of the extended portion can be adjusted.

In the method for manufacturing in the present invention, the sheet-like structure further contains a sewn area formed on a free end side of the extended portion, which contains a specified thread member. In the step of forming the loosened portion, each length of the plural linear portions in a specified direction is set longer than each length of the plural sheet members in the specified direction arranged so as to be in contact with each of the plural linear portions in the step of arranging. In this way, the cord member can be sewn onto the sheet member by sewing along the linear portions in the step of sewing, while the sheet members are arranged in contact with the linear portions, and the areas sewn with a specified thread member can be formed on the portions extending from the sheet members in contact with the linear portions. A specified portion of the sewn areas of the sheet member are cut, thereby enabling sewn areas containing the specified thread member to be formed on free ends of the extended portions of the sheet members, which lie adjacent to the above sheet member.

In the method for manufacturing in the present invention, the sheet member is a sheet-like absorbing member containing a specified absorbing layer with liquid absorbability coated with a surface material of thin film, and the method for manufacturing in the present invention further contains a step of forming the sheet member in which the absorbing layer is coated with the surface material. This allows a sheet-like absorbing member to be formed by applying a surface material to the fibrous absorbing layer for preventing unraveling of the fibrous absorbing layer, and enables the above-mentioned cord member to be sewed onto the absorbing member formed in a sheet-like form.

The method for manufacturing a sheet-like structure of the present invention can be implemented by the above-mentioned manufacturing system or apparatus for the sheet-like structure. The details and operations of each apparatus in each step are as described in the manufacture of sheet-like structure above.

The manufacturing system and the method for manufacturing of the present invention can be used for manufacturing sheet-like structures, such as clothes, covers, tents and absorbing media for tampons.

What is claimed is:

1. A manufacturing system for a tampon comprising a sheet member and a cord member that is sewn onto a surface of the sheet member with a thread member and has an extended portion extending from an outer edge of the surface, the extending portion having a non-sewn area without the thread member, the manufacturing system comprising:
    a loosened portion forming apparatus to form a plurality of substantially U-shaped loosened portions for a cord member reeled out in a specified direction, the plurality of loosened portions extending in a direction different from a the specified direction, and a plurality of substantially linear portions which connects adjacent pairs of the plurality of loosened portions of the cord member respectively;
    an arranging apparatus to allow a plurality of sheet members to be in contact with the plurality of linear portions of the cord member formed by the loosened portion forming apparatus;
    a sewing apparatus to sew with a thread member each of the plurality of sheet members and each of the plurality of linear portions of the cord member in contact with each other arranged by the arranging apparatus;
    a thread member cutting apparatus to cut thread connecting portions that comprise parts of the thread member connecting adjacent pairs of the plurality of sheet members on which the plurality of linear portions of the cord member is sewn by the sewing apparatus; and
    a cord member cutting apparatus to cut cord connecting portions that comprise parts of the cord member connecting adjacent pairs of the plurality of sheet members at a specified position.

2. The manufacturing system according to claim 1, further comprising a cord member reeling-out apparatus to reel out the cord member in the specified direction.

3. The manufacturing system according to claim 1, wherein the loosened portion forming apparatus is configured to arrange the plurality of linear portions substantially linearly at specified intervals.

4. The manufacturing system according to claim 3, wherein the sewing apparatus is configured to sew each of the plurality of linear portions of the cord member, arranged substantially linear at the specified intervals by the loosened portion forming apparatus, onto each of the plurality of sheet members along a straight line formed by the plurality of linear portions of the cord member.

5. A manufacturing system for a sheet-like structure comprising a sheet member and a cord member that is sewn onto a surface of the sheet member with a thread member and has an extended portion extending from an outer edge of the surface, the extended portion having a non-sewn area without the thread member, the manufacturing system comprising;
    a loosened portion forming apparatus to form a plurality of substantially U-shaped loosened portions for a cord member reeled out in a specified direction, the plurality of loosened portions extending in a direction different from the specified direction, and a plurality of substantially linear portions which connects adjacent pairs of the plurality of loosened portions of the cord member respectively;
    an arranging apparatus to allow a plurality of sheet members to be in contact with the plurality of linear portions of the cord member formed by the loosened portion forming apparatus;
    a sewing apparatus to sew with a thread member each of the plurality of sheet members and each of the plurality of linear portions of the cord member in contact with each other arranged by the arranging apparatus;
    a thread member cutting apparatus to cut thread connecting portions that comprise parts of the thread member connecting adjacent parts of the plurality of sheet members on which the plurality of linear portions of the cord member is sewn by the sewing apparatus; and
    a cord member cutting apparatus to cut cord connecting portions that comprise parts of the cord member connecting adjacent pairs of the plurality of sheet members at a specified position, wherein the cord member cutting apparatus comprises an apparatus configured to extend the cord connecting portions substantially linearly.

6. A manufacturing system for a sheet-like structure comprising a sheet member and a cord member that is sewn onto a surface of the sheet member with a thread member and has an extended portion extending from an outer edge of the surface, the extended portion having a non-sewn area without the thread member, the manufacturing system comprising;
    a loosened portion forming apparatus to form a plurality of substantially U-shaped loosened portions for a cord member reeled out in a specified direction, the plurality of loosened portions extending in a direction different from the specified direction, and a plurality of substantially linear portions which connects adjacent pairs of the plurality of loosened portions of the cord member respectively;
    an arranging apparatus to allow a plurality of sheet members to be in contact with the plurality of linear portions of the cord member formed by the loosened portion forming apparatus;
    a sewing apparatus to sew with a thread member each of the plurality of sheet members and each of the plurality of linear portions of the cord member in contact with each other arranged by the arranging apparatus;
    a thread member cutting apparatus to cut thread connecting portions that comprise parts of the thread member connecting adjacent parts of the plurality of sheet members on which the plurality of linear portions of the cord member is sewn by the sewing apparatus; and a cord member cutting apparatus to cut cord connection portions that comprise parts of the cord member c6nnecting adjacent pairs of the plurality of sheet members at a specified position, wherein the sheet-like structure further comprises a sewn area including the thread member on a free end side of the extended portion and, the loosened portion forming apparatus is configured to allow a length of each of the plurality of linear portions of the cord member to be longer with respect to the specified direction than a length of each of the plurality of sheet members which is rendered to be in contact with each of the plurality of linear portions of the cord member by the arranging apparatus.

7. A manufacturing system for a sheet-like structure comprising a sheet member and a cord member that is sewn onto a surface of the sheet member with a thread member and has an extended portion extending from an outer edge of the surface, the extended portion having a non-sewn area without the thread member, the manufacturing system comprising:

a loosened portion forming apparatus to form a plurality of substantially U-shaped loosened portions for a cord member reeled out in a specified direction, the plurality of loosened portions extending in a direction different from the specified direction, and a plurality of substantially linear portions which connects adjacent pairs of the plurality of loosened portions of the cord member respectively;

an arranging apparatus to allow a plurality of sheet members to be in contact with the plurality of linear portions of the cord member formed by the loosened portion forming apparatus;

a sewing apparatus to sew with a thread member each of the plurality of sheet members and each of the plurality of linear portions of the cord member in contact with each other arranged by the arranging apparatus;

a thread member cutting apparatus to cut thread connecting portions that comprise parts of the thread member connecting adjacent parts of the plurality of sheet members on which the plurality of linear portions of the cord member is sewn by the sewing apparatus; and a cord member cutting apparatus to cut cord connection portions that comprise Darts of the cord member connecting adjacent pairs of the plurality of sheet members at a specified position, wherein the sheet member comprises a sheet-like absorbing member comprising a liquid absorbable layer coated with a surface material of thin film, and the manufacturing system further comprises a sheet-like member forming apparatus to apply the surface material to the liquid absorbable layer.

8. A method for manufacturing a tampon comprising a sheet member and a cord member that is sewn onto a surface of the sheet member with a thread member and has an extended portion extending from an outer edge of the surface, the extended portion having a non-sewn area without the thread member, the method comprising:

forming a plurality of substantially U-shaped loosened portions for a cord member reeled out in a specified direction, the plurality of loosened portions extending in a direction different from the specified direction, and a plurality of linear portions which substantially linearly connects adjacent pairs of the plurality of loosened portions of the cord member, respectively;

allowing a plurality of sheet members to be in contact with the plurality of linear portions of the cord member;

sewing with a thread member each of the plurality of sheet members and each of the plurality of linear portions of the cord member in contact with each other;

cutting thread connecting portions that comprise parts of the thread member connecting adjacent pairs of the plurality of sheet members on which the plurality of linear portions of the cord member is sewn; and cutting cord connecting portions that comprise parts of the cord member connecting adjacent pairs of the plurality of sheet members at a specified position.

9. The method for manufacturing a sheet-like structure according to claim 8, further comprising reeling out the cord member in the specified direction.

10. The method according to claim 8, wherein forming the plurality of loosened portions comprises arranging the plurality of linear portions of the cord member substantially linearly at specified intervals.

11. The method according to claim 10, wherein each of the plurality of linear portions of the cord member, arranged substantially linearly at the specified intervals forming the plurality of loosened portions, is sewn onto each of the plurality of sheet members along a straight line formed by the plurality of linear portions of the cord member in sewing.

12. A method for manufacturing a sheet-like structure comprising a sheet member and a cord member that is sewn onto a surface of the sheet member with a thread member and has an extended portion extending from an outer edge of the surface, the extended portion having a non-sewn area without the thread member, the method comprising:

forming a plurality of substantially U-shaped loosened portions for a cord member reeled out in a specified direction, the plurality of loosened portions extending in a direction different from the specified direction, and a plurality of linear portions which substantially linearly connects adjacent pairs of the plurality of loosen portions of the cord member, respectively;

allowing a plurality of sheet members to be in contact with the plurality of linear portions of the cord member;

sewing with a thread member each of the plurality of sheet members and each of the plurality of linear Portions of the cord member in contact with each other;

cutting thread connecting portions that comprise parts of the thread member connecting adjacent pairs of the plurality of sheet members on which the plurality of linear portions of the cord member is sewn; and cutting cord connecting portions that comprise carts of the cord member connecting adjacent pairs of the plurality of sheet members at a specified position, wherein cutting the cord connecting portions of the cord member comprises extending the cord connecting portions substantially linearly.

13. A method for manufacturing a sheet-like structure comprising a sheet member and a cord member that is sewn onto a surface of the sheet member with a thread member and has an extended portion extending from an outer edge of the surface, the extended portion having a non-sewn area without the thread member, the method comprising:

forming a plurality of substantially U-shaped loosened portions for a cord member reeled out in a specified direction, the plurality of loosened portions extending in a direction different from the specified direction, and a plurality of linear portions which substantially linearly connects adjacent pairs of the plurality of loosened portions of the cord member, respectively;

allowing a plurality of sheet members to be in contact with the plurality of linear portions of the cord member;

sewing with a thread member each of the plurality of sheet members and each of the plurality of linear portions of the cord member in contact with each other;

cutting thread connecting portions that comprise parts of the thread member connecting adjacent pairs of the plurality of sheet members on which the plurality of linear portions of the cord member is sewn; and cutting cord connecting portions that comprise parts of the cord member connecting adjacent pairs of the plurality of sheet members at a specified position, wherein the sheet-like structure further comprises a sewn area including the thread member on a free end side of the extended portion, and wherein forming the plurality of loosened portions comprises allowing a length of each of the plurality of linear portions of the cord member to be longer with respect to the specified direction than a length of each of the plurality of sheet members, which is rendered to be in contact with each of the plurality of linear portions of the cord member.

14. A method for manufacturing a sheet-like structure comprising a sheet member and a cord member that is sewn onto a surface of the sheet member with a thread member and has an extended portion extending from an outer edge of the surface, the extended portion having a non-sewn area without the thread member, the method comprising:

forming a plurality of substantially U-shaped loosened portions for a cord member reeled out in a specified direction, the plurality of loosened portions extending in a direction different from the specified direction, and a plurality of linear portions which substantially linearly connects adjacent pairs of the plurality of loosened portions of the cord member, respectively;

allowing a plurality of sheet members to be in contact with the plurality of linear portions of the cord member;

sewing with a thread member each of the plurality of sheet members and each of the plurality of linear portions of the cord member in contact with each other;

cutting thread connecting portions that comprise parts of the thread member connecting adjacent pairs of the plurality of sheet members on which the plurality of linear portions of the cord member is sewn; and cutting cord connecting portions that comprise parts of the cord member connecting adjacent pairs of the plurality of sheet members at a specified position, wherein the sheet member is comprises a sheet-like absorbing member comprising a liquid absorbable layer coated with a surface material in a form of thin film, and the method further comprises applying the surface material to the liquid absorbable layer.

* * * * *